United States Patent
Puckett

(10) Patent No.: US 7,434,468 B2
(45) Date of Patent: Oct. 14, 2008

(54) POROSITY REFERENCE STANDARD FOR ULTRASONIC INSPECTION OF COMPOSITE MATERIALS

(75) Inventor: Edward L. Puckett, Renton, WA (US)

(73) Assignee: The Boeing Company, Chicago, IL (US)

( * ) Notice: Subject to any disclaimer, the term of this patent is extended or adjusted under 35 U.S.C. 154(b) by 422 days.

(21) Appl. No.: 11/263,811

(22) Filed: Oct. 31, 2005

(65) Prior Publication Data

US 2007/0095141 A1    May 3, 2007

(51) Int. Cl.
*G01H 11/00*    (2006.01)
(52) U.S. Cl. .............................. 73/649; 73/1.86; 73/627
(58) Field of Classification Search ................... 73/649, 73/1.03, 1.86, 604, 620, 627
See application file for complete search history.

(56) References Cited

U.S. PATENT DOCUMENTS

| | | | |
|---|---|---|---|
| 6,426,274 B1 * | 7/2002 | Tayanaka ..................... 438/458 |
| 6,684,701 B2 * | 2/2004 | Dubois et al. ................. 73/579 |
| 7,216,544 B2 * | 5/2007 | Vaccaro et al. ................ 73/620 |
| 2006/0234391 A1 * | 10/2006 | Weiss et al. .................. 436/518 |
| 2007/0006651 A1 * | 1/2007 | Kruger et al. ................. 73/579 |
| 2007/0119256 A1 * | 5/2007 | Vaccaro et al. ................ 73/649 |

* cited by examiner

*Primary Examiner*—Hezron E. Williams
*Assistant Examiner*—Jacques M. Saint-Surin
(74) *Attorney, Agent, or Firm*—Duke W. Yee; Dennis R. Plank; Gerald H. Glanzman

(57) ABSTRACT

A porosity reference standard for ultrasonic inspection of composite materials includes a right prism manufactured from a solid isotropic material and a porosity created within the right prism. The porosity reference standard may be a glass block that encloses a plurality of simulated voids created through laser etching. The porosity reference standard may be manufactured by using a sub surface laser engraving process. By creating a porosity within the glass block, the level of the porosity can be exactly determined and is spatially constant over a desired area within the glass block. The laser-etched porosity reference standard is suitable for, but not limited to, ultrasonic porosity inspection of composite laminate parts, such as wings, empennage and fuselage skins, sub-skin structures, frames stringer, and shear ties, used in the aircraft airframe industry, both commercial and defense.

20 Claims, 3 Drawing Sheets

POROSITY REFERENCE STANDARD FOR ULTRASONIC INSPECTION OF COMPOSITE MATERIALS

BACKGROUND OF THE INVENTION

The present invention generally relates to reference standards and ultrasonic inspection methods and, more particularly, to a laser-etched porosity reference standard for ultrasonic inspection of composite materials and to an ultrasonic porosity standardization process.

The use of fiber-reinforced composite laminate structure as a structural element is rapidly increasing, for example, in the aerospace industry, due to the weight savings, which lead to a reduction in aircraft fuel consumption, and the improvement in fatigue life and corrosion control that can be achieved by using fiber-reinforced composite materials. Typically, fiber-reinforced composite materials contain a strong and stiff fiber, such as a carbon fiber, embedded in a softer matrix material, such as a resin. The resin is used as a binding agent to hold the fibers together while the fibers provide the strength. Laminated composites are constructed of many layers of fiber-reinforced materials. Fiber-reinforced polymer matrix composites, such as graphite/epoxy and carbon/cyanate ester are now the materials of choice for spacecraft and launch vehicle structures and subsystems such as optical benches, instruments, and antennas. Key components, such as wings, empennage and fuselage skins, for example, in commercial and military aircraft, are now being constructed almost exclusively of this material. Fiber-reinforced polymer matrix composites are also widely used, for example, in sports, industrial, and medical equipment. With more and more critical structure being made of fiber-reinforced composite laminates, ways to assure good quality construction are needed more than ever before. Consequently, inspecting these composite structures is a critical element in assuring the material quality needed for their application, for example in a commercial airplane.

Laminated composite materials undergo non-destructive testing procedures, such as ultrasonic and radiographic inspection, during aircraft manufacturing, maintenance, and repair. Common aircraft applications include, for example, porosity testing, thickness testing, and crack detection of the aircraft airframe. Ultrasonic testing introduces high frequency sound waves into the test material to detect subsurface discontinuities. Transducers are used both to transmit and receive sound energy into and from test material. In the process, high frequency sound in the order of 500 KHz (kilohertz) to 10 MHz (megahertz) is sent, for example, into a composite laminate and echoes from the laminate are then measured in the time domain and the amplitude domain to determine the materials quality. Through-transmission and pulse-echo techniques are most commonly used in the aircraft airframe industry, both commercial and defense. Some advantages of the ultrasonic testing method include high penetrating capability, high sensitivity and resolution, portability, single surface accessibility, and the immediate interpretation of test results.

Porosity is a known detrimental material condition that includes a plurality of voids in the composite material caused by trapped or evolved gases which may be caused by improper processing, such as improper curing of the composite material. Currently, millions of dollars are spent on ultrasonic systems designed to detect and quantify porosity in composite laminate parts manufactured, for example, from graphite/epoxy composites. The ultrasonic inspection of composite laminates takes advantage of the fact that porosity does not block ultrasound, like, for example, a delamination does, but scatters and attenuates the ultrasound. Consequently, by measuring the amount of attenuation an estimate of the degree of porosity can be obtained for correlation with manufacturing specifications. Typically, attenuation curves are produced to match ultrasonic attenuation on the inspected composite laminate part with actual porosity levels. Unfortunately, such attenuation curves are individual to the interrogating transducers and ultrasonic machine, and, therefore, different instrumentation at different inspection sites may produce different results. Consequently, the part might pass the specification tolerance at one inspection site but may fail at another.

To mitigate the above problem, sets of porosity reference standards are manufactured for use at each inspection site. These porosity reference standards are necessary to compare the ultrasonic response between the inspected part and a known porosity level tested with a particular ultrasonic machine. Typically, these sets of porosity reference standards include 30 to 40 panels, having a size of about 4 by 4 inches with varying thicknesses, for a variety of porosity levels. Currently, the panels are made out of the same fiber-reinforced composite material as the part to be inspected, for example, graphite/epoxy. Generally, during the manufacturing process of the panels, the cure parameters are altered to produce varying degrees of porosity. Since the porosity levels of a panel typically vary spatially due to the inherent anisotropy of the fiber-reinforced material, the ultrasonic attenuation values must be averaged over the area of the panel. Frequently, destructive testing, for example, by cross-sectioning, polishing and optical analyzing, of an area of similar attenuation values in the panel is performed so that the exact cross-sectional porosity content can be identified for correlation with the attenuation value. This is an arduous and expensive process. Since the number of suppliers of fiber-reinforced material parts that perform on site porosity inspection and evaluation of the manufactured parts is growing, it is necessary to manufacture more sets of porosity reference standards to distribute to each supplier, further increasing manufacturing cost and time.

As can be seen, there is a need for porosity reference standards that allow standardization of ultrasonic inspection equipment used for inspection of fiber-reinforced composite materials and enable a consistent porosity inspection process. Furthermore, there is a need for a lower-cost, reliable way of producing porosity reference standards. There has, therefore, arisen a need to provide a porosity reference standard that can be used in ultrasonic porosity inspection processes for composite laminates, that provides a reliable, common reference for porosity values, that enables consistent and accurate porosity evaluation of porosity levels in composite materials, and that can replace existing expensive composite porosity reference standards. There has further arisen a need to provide a method for producing voids within a material to manufacture a porosity reference standard, which has a constant level of porosity over an area, at a lower cost and with a reduced machining time compared to existing standards.

SUMMARY OF THE INVENTION

In one aspect of the present invention, a porosity reference standard for ultrasonic inspection of composite materials comprises a right prism manufactured from a solid isotropic material, and a porosity created within the right prism. The level of the created porosity is spatially uniform.

In another aspect of the present invention, a porosity reference standard for ultrasonic inspection of composite materials comprises a rectangular prism manufactured from a solid isotropic material, and a first plurality of simulated voids created within the first area to form a spatially uniform porosity of a first level. The rectangular prism includes a first area and a second area. The second area is an undisturbed area with no simulated voids created within.

In a further aspect of the present invention, a porosity standardization process for ultrasonic inspection of composite materials comprises the steps of: manufacturing a porosity reference standard to include a porosity of a first spatially uniform level created within; and comparing the attenuation of an ultrasonic signal sent into said porosity reference standard with provided attenuation curves provided for the composite material of a part to be tested.

These and other features, aspects and advantages of the present invention will become better understood with reference to the following drawings, description and claims.

DETAILED DESCRIPTION OF THE INVENTION

Figure 1A:
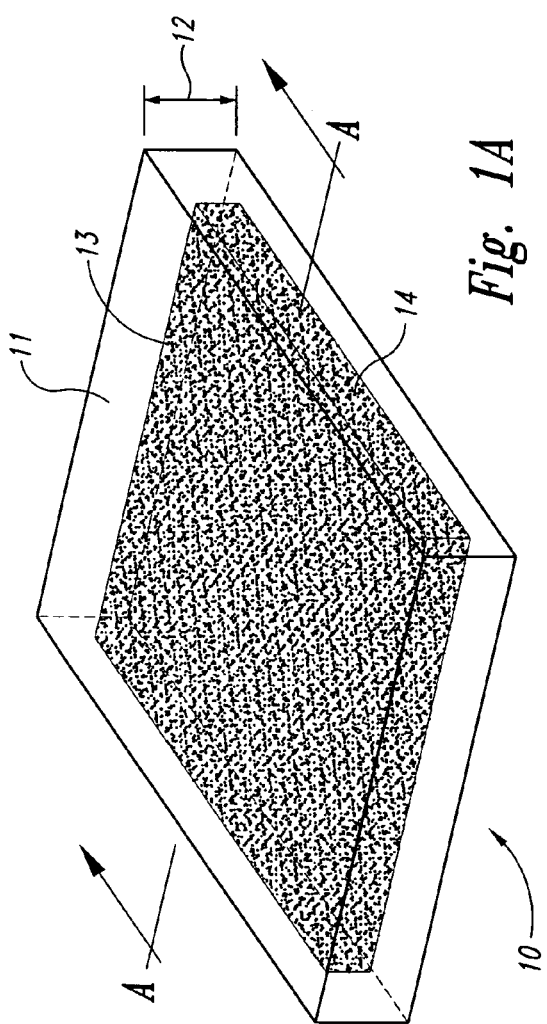
FIG. 1a is perspective view of a porosity reference standard according to one embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Broadly, the present invention provides a laser-etched porosity reference standard for ultrasonic inspection of composite materials. In one embodiment the present invention provides a glass block that encloses a created porosity. An embodiment of the present invention provides a laser-etched porosity reference standard that is suitable for, but not limited to, ultrasonic porosity inspection of composite laminate parts, such as wings, empennage and fuselage skins, sub-skin structures, frames, and shear ties, used in the aircraft airframe industry, both commercial and defense.

In one embodiment, the present invention provides a porosity reference standard for ultrasonic inspection of composite materials, such as graphite/epoxy, that is a block manufactured out of an isotropic medium, such as glass, and that has a created porosity embedded. By creating a porosity within the glass block, the level of the porosity can be exactly determined and is spatially constant over a desired area within the glass block, which can not be achieved in prior art porosity reference standards manufactured out of the same composite material as the parts to be investigated, where the porosity is created by varying the parameters of the curing process. By providing a glass block as in one embodiment of the present invention instead of a prior art composite material block, the need to create a standard for each composite material to be tested can be eliminated.

In one embodiment, the present invention utilizes a sub surface laser engraving process (SSLE) to manufacture the porosity reference standard. By using the sub surface laser engraving process, pseudo randomly distributed simulated voids can be created within a clear solid glass article, such as a glass block, that form a spatially uniform level of porosity in contrast to spatially varying porosity levels that are produced using the prior art approach of altering the cure parameters of the composite material used for manufacturing a typical prior art porosity reference standard. The sub surface laser engraving process as in one embodiment of the present invention has further the advantage over prior art techniques that simulated voids, which provide the scattering and attenuation of ultrasonic energy much like actual voids would in actual composite structures, can be created in a closed volume, such as a glass block, in contrast to creating cavities that must have an opening to the surface. The ability to design simulated voids in a 3D CAD (computer-aided design) model, as in one embodiment of the present invention, leads to an ability to precisely replicate the ultrasonic characteristics of actual porosity voids, for example, the scattering and attenuation of ultrasonic energy, while arranging the simulated voids in an evenly distributed manner, such as a repeating pattern that is randomized enough to avoid complications related to a strictly repetitive pattern. When creating a typical prior art porosity reference standard out of a composite material, such as graphite/epoxy, by altering the cure parameters, such as the cure pressure, the obtained porosity level is not exactly predictable and the level of porosity is most likely not uniform within the standard, which may lead to inconsistencies when standardizing the ultrasonic equipment. These problems may be avoided by using the sub surface laser engraving process to manufacture the glass porosity reference standard having a laser-etched porosity within, as in one embodiment of the present invention.

Figure 1C:
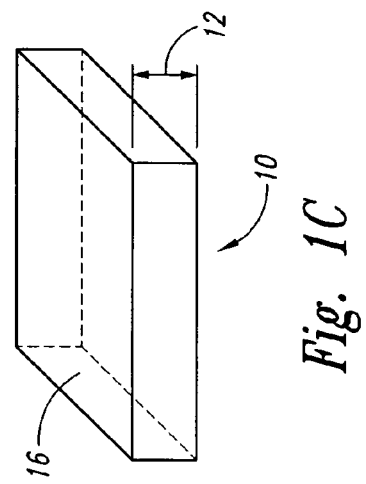
FIG. 1c is a perspective view of an unaltered porosity reference standard according to one embodiment of the present invention.
Figure 1B:
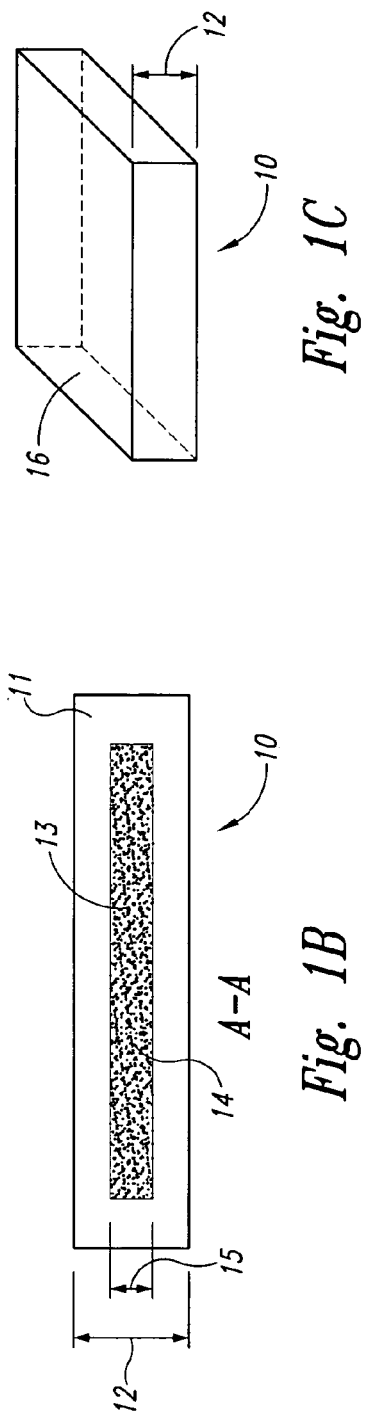
FIG. 1b is a cross-sectional view taken along line A-A of a laser-etched porosity reference standard according to one embodiment of the present invention.

Referring now to FIGS. 1a, 1b, and 1c a porosity reference standard 10 for ultrasonic inspection of composite materials is illustrated according to one embodiment of the present invention. The porosity reference standard 10 may have the shape of a right prism having a rectangular or square base, such as block 11. The porosity reference standard 10 may have a thickness 12. The porosity reference standard 10 may be manufactured from a solid isotropic material, such as clear glass. Therefore, the block 11 may be, for example, a glass block. It may be useful to manufacture the porosity reference standard 10 from a high quality, clear, colorless glass, such as crystal, a colorless glass made out of almost pure silica. Crystal is a homogeneous solid having a highly regular atomic structure and may, therefore, be a suitable material for the ultrasonic inspection process and the sub surface laser engraving process discussed below.

The porosity reference standard 10 may include a created porosity 13 embedded within the block 11 (FIGS. 1a and 1b). The created porosity 13 may be formed from a plurality of simulated voids 14 that are etched into the solid isotropic material using a laser. The simulated voids 14 may be a series of very small fractures that may closely replicate the ultrasonic characteristics and, therefore, the ability to scatter ultrasonic energy, of voids typically embedded within composite laminates. The simulated voids 14 may be pseudo randomly distributed within the block 11 such that they may have a repeating pattern, but one that is randomized enough to avoid complications connected with a strictly repetitive pattern. The number of simulated voids 14 created within the block 11 may be chosen according to a desired porosity level. The simulated voids 14 may be arranged so that the level of the created porosity 13 is spatially uniform. Different levels of porosity 13 may be simulated by increasing or decreasing the number of simulated voids 14 created within the block 11. Different levels of porosity 13 may further be simulated by changing the size of the simulated voids 14 created within the block 11. Different levels of porosity 13 may still further be simulated by changing the thickness 12 of the block 11 and the thickness 15 of the porosity 13 created within.

In order to ensure accurate standardization of ultrasonic instrumentation at testing sites at least two porosity reference standards 10 may be needed. One porosity reference standard 10 may be an unaltered glass block 16, as shown in FIG. 1c. Another porosity reference standard 10 may be a block 11 that has a porosity 13 of a certain level created within. Additional blocks 11 having different levels of porosity created within may be provided for increased quality of standardization, which may be required by certain manufacturing specifications. Instead of manufacturing at least two porosity reference standards 10 a block 21 including at least two areas of different levels of porosity 13, as illustrated in FIG. 2, may be provided.

Figure 2:
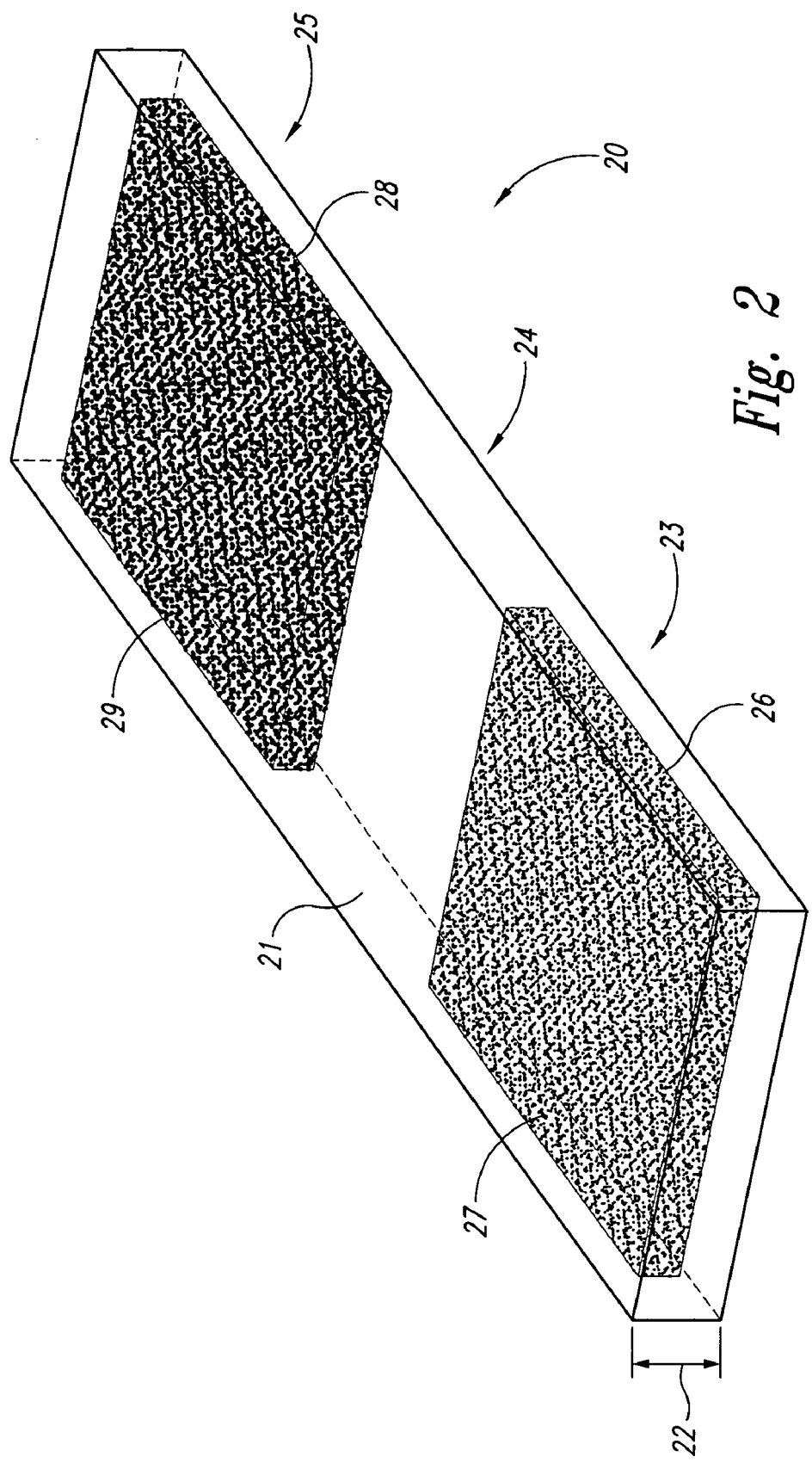
FIG. 2 is a perspective view of a laser-etched porosity reference standard according to another embodiment of the present invention.

Referring now to FIG. 2, a laser-etched porosity reference standard 20 for ultrasonic inspection of composite materials is illustrated according to another embodiment of the present invention. The porosity reference standard 20 may have the shape of a rectangular prism, such as block 21. The porosity reference standard 20 may have a thickness 22. The porosity reference standard 20 may be manufactured from a solid isotropic material, such as clear glass, as discussed in connection with FIGS. 1a, 1b, and 1c. The block 21 may include three areas, area 23, area 24, and area 25. A plurality of simulated voids 26 may be created within the area 23 to form a spatially uniform porosity 27 of a first level (as described above in connection with FIGS. 1a and 1b). Area 24 of the block 21 may be an undisturbed area with no simulated voids 26 or 28 created within. A plurality of simulated voids 28 may be created within the area 25 to form a spatially uniform porosity 29 of a second level that is different from the first level of porosity 27 created in area 23.

Only one laser-etched porosity reference standard 20 may need to be provided to ensure accurate standardization of ultrasonic instrumentation at testing sites. Furthermore, a laser-etched porosity reference standard 20 that includes only two areas, for example, area 23 and area 24 or area 24 and area 25, may be sufficient to ensure accurate standardization of ultrasonic instrumentation. An undisturbed area 24 may be always needed in connection with an area, such as area 23 or area 25, having a porosity, such as porosity 27 or 29, respectively, created within. For certain applications it may further be necessary to manufacture the porosity reference standard 20 to include more than three areas, such as areas 23, 24, and 25, that have a different level of porosity, such as porosities 27 and 29.

Figure 3:
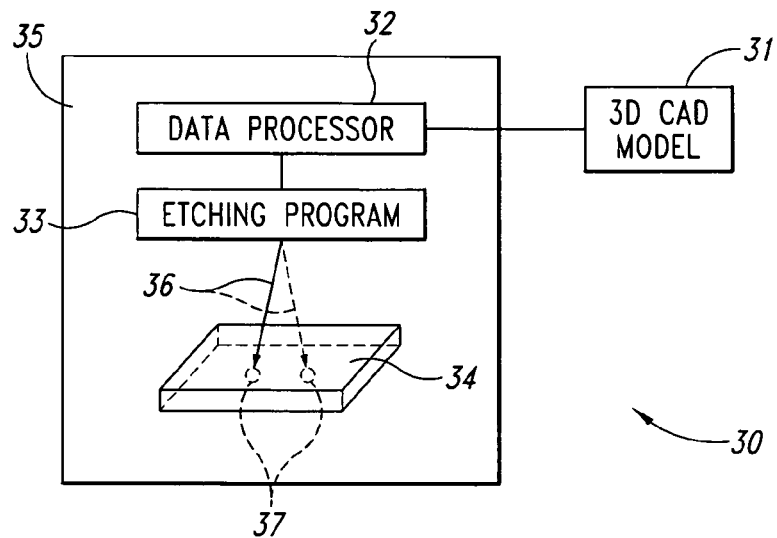
FIG. 3 is a system block diagram for a process for manufacturing a porosity reference standard for ultrasonic inspection of composite materials according to another embodiment of the present invention.

The porosity reference standards 10 and 20, as illustrated in FIGS. 1a and 2, respectively, may be manufactured using a sub surface laser engraving process 30 as illustrated in FIG. 3 according to another embodiment of the present invention. The sub surface laser engraving process 30 may be used to etch three-dimensional images, such as the simulated voids 14 (FIG. 1) or the simulated voids 26 and 28 (FIG. 2) inside a solid isotropic medium 34, such as the block 11 (FIG. 1a) or the block 21 (FIG. 2). The simulated voids forming a porosity within a composite laminate may be simulated in a three-dimensional CAD (computer-aided design) model 31. The three-dimensional CAD model 31 may then be processed, cleaned, and converted into a point cloud by a data processor 32 of a laser engraving machine 35. The point cloud may be the conversion of the three-dimensional CAD model 31 into a pixel resolution, for example, of about 40,000 to 60,000 points. The processed three-dimensional CAD model 31 of the simulated voids may be exported into the etching program 33. The solid isotropic medium 34, such as the block 11 (FIG. 1a) or the block 21 (FIG. 2), may be placed in the laser engraving machine 35. During the laser etching process, a laser beam 36 penetrates the solid isotropic medium 34 to create tiny cracks, such as points or dots, in the solid isotropic medium 34, i.e. below the surface. The laser beam 36 may be directed according to the processed three-dimensional computer aided design model 31. The energy from the laser 36 may pass through a lens such that no other point in the solid isotropic medium 34 is affected than the focal point. After repeating to penetrate the solid isotropic medium 34 to create tiny cracks many times, thousands of little cracks may create isolated simulated voids 37 within the solid isotropic medium 34, and, therefore, within a closed volume. Laser engraving machines 35 are commercially available from a variety of manufacturers, for example, CrystalixUSA, Las Vegas, Nev., U.S.A.

The sub surface laser engraving process 30 may enable the precise creation of pseudo randomly distributed simulated voids 37 within a solid isotropic medium 34, such as glass. In the three-dimensional CAD model 31, voids typically found in composite laminates, such as graphite/epoxy, may be closely replicated and the images of the simulated voids 37 may be arranged to form a spatially uniform level of porosity, such as porosity 13 (FIGS. 1a and 1b) or porosities 27 and 29 (FIG. 2). Consequently, ultrasonic characteristics of porosities of composite laminates may be closely simulated. When exposed to ultrasonic energy, the simulated voids 37 scatter the ultrasound in a similar manner as a porosity in composite laminate parts does, which leads to the attenuation of the ultrasonic signal.

Figure 4:
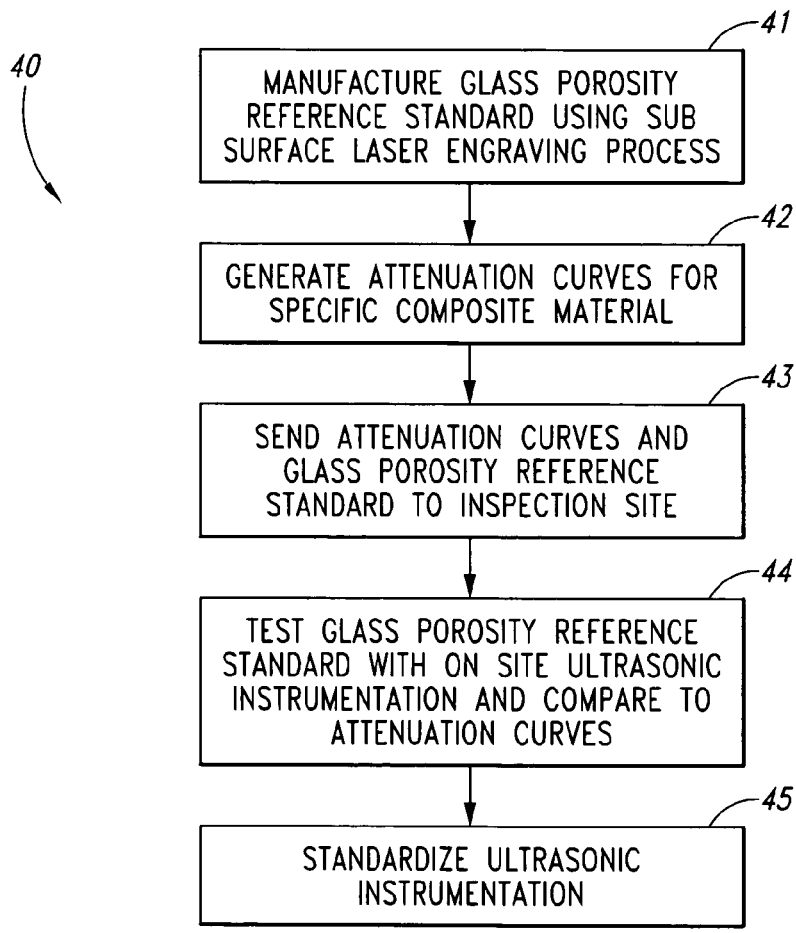
FIG. 4 is a flow chart of an porosity standardization process for ultrasonic inspection of composite materials according to another embodiment of the present invention.

Referring now to FIG. 4, a porosity standardization process 40 for ultrasonic inspection of composite materials is illustrated according to another embodiment of the present invention. The porosity standardization process 40 may include manufacturing a glass porosity reference standard, such as at least two porosity reference standards 10 (FIG. 1a and 1c) or the porosity reference standard 20 (FIG. 2), using the sub surface laser engraving process 30 (FIG. 3), in step 41. In step 42, ultrasonic attenuation curves for a specific composite material, such as graphite/epoxy, may be generated using a set of prior art composite porosity reference standards manufactured from the same composite materials as the parts to be tested. The created glass porosity reference standard, such as at least two porosity reference standards 10 (FIGS. 1a and 1c) or the porosity reference standard 20 (FIG. 2), and the attenuation curves may then be sent to an inspection site where composite laminate parts are inspected using ultrasonic methods, in step 43. The glass porosity reference standard, such as at least two porosity reference standards 10 (FIGS. 1a and 1c) or the porosity reference standard 20 (FIG. 2), may be tested with the on site ultrasonic instrumentation and the attenuation of the ultrasonic signal sent into the porosity reference standard may be compared with the attenuation curves, in step 44. The on site ultrasonic instrumentation may now be standardized accordingly, in step 45. This may include obtaining a correction factor for the ultrasonic instrumentation, which is now ready for the inspection of the composite laminate parts, such as wings, empennage and fuselage skins of an aircraft.

The glass porosity reference standard, such as at least two porosity reference standards 10 (FIGS. 1*a* and 1*b*) or the porosity reference standard 20 (FIG. 2), may then further be used to ensure that the ultrasonic equipment is stable. By introducing the glass porosity reference standard, such as at least two porosity reference standards 10 (FIGS. 1*a* and 1*c*) or the porosity reference standard 20 (FIG. 2), the need to send out a set of the expensive prior art porosity reference standards for each composite material to be tested to each inspection site may be eliminated and a consistent ultrasonic porosity inspection process of composite laminate parts may be enabled.

It should be understood, of course, that the foregoing relates to exemplary embodiments of the invention and that modifications may be made without departing from the spirit and scope of the invention as set forth in the following claims.

I claim:

1. A porosity reference standard for ultrasonic inspection of composite materials, comprising:
   a right prism manufactured from a solid isotropic material; and
   a porosity created within said right prism, wherein said porosity is formed from a plurality of simulated voids in said solid isotropic material, and wherein a level of said created porosity is spatially uniform.

2. The porosity reference standard for ultrasonic inspection of composite materials of claim 1, wherein said porosity is formed from a plurality of simulated voids that are etched into said solid isotropic material using a laser and that are pseudo randomly distributed within said right prism.

3. The porosity reference standard for ultrasonic inspection of composite materials of claim 2, wherein said simulated voids closely replicate the ultrasonic characteristics of voids embedded within said composite materials.

4. The porosity reference standard for ultrasonic inspection of composite materials of claim 1, wherein different levels of said porosity are created by changing the number of said simulated voids.

5. The porosity reference standard for ultrasonic inspection of composite materials of claim 1, wherein different levels of said porosity are created by changing the size of said simulated voids.

6. The porosity reference standard for ultrasonic inspection of composite materials of claim 1, wherein said right prism has a thickness, and wherein different levels of said porosity are created by changing said thickness of said right prism.

7. The porosity reference standard for ultrasonic inspection of composite materials of claim 1, wherein said right prism has a rectangular base.

8. The porosity reference standard for ultrasonic inspection of composite materials of claim 1, wherein said right prism has a square base.

9. The porosity reference standard for ultrasonic inspection of composite materials of claim 1, wherein said solid isotropic material is crystal.

10. The porosity reference standard for ultrasonic inspection of composite materials of claim 1, wherein said solid isotropic material is clear glass.

11. A porosity reference standard for ultrasonic inspection of composite materials, comprising:
    a rectangular prism manufactured from a solid isotropic material, wherein said rectangular prism includes a first area and a second area, wherein said second area is an undisturbed area with no simulated voids created within; and
    a first plurality of simulated voids created within said first area to form a spatially uniform porosity of a first level.

12. The porosity reference standard for ultrasonic inspection of composite materials of claim 11, wherein said rectangular prism further includes at least one additional area, and wherein at least one additional plurality of simulated voids is created within said additional area to form a spatially uniform porosity of at least one additional level.

13. The porosity reference standard for ultrasonic inspection of composite materials of claim 11, wherein said rectangular prism is a clear glass block.

14. The porosity reference standard for ultrasonic inspection of composite materials of claim 11, wherein said first plurality of simulated voids and said at least one additional plurality of simulated voids is created within said rectangular prism using a sub surface laser engraving process.

15. The porosity reference standard for ultrasonic inspection of composite materials of claim 14, wherein said sub surface laser engraving process uses a laser beam to penetrate said solid isotropic material and to create cracks below the surface of said rectangular prism, wherein a plurality of said cracks creates said simulated voids.

16. The porosity reference standard for ultrasonic inspection of composite materials of claim 15, wherein said laser beam is activated according to a three-dimensional computer-aided design model, wherein said computer-aided design model replicates voids forming a porosity within said composite materials.

17. A porosity standardization process for ultrasonic inspection of composite materials, comprising the steps of:
    manufacturing a porosity reference standard to include a porosity of a first spatially uniform level created within, wherein said porosity is formed from a plurality of simulated voids in said porosity reference standard; and
    comparing the attenuation of an ultrasonic signal sent into said porosity reference standard with attenuation curves provided for the composite material of a part to be tested.

18. The porosity standardization process for ultrasonic inspection of composite materials of claim 17, further including the steps of:
    manufacturing said porosity reference standard from a glass block;
    creating said simulated voids within said glass block using a sub surface laser engraving process to manufacture said a glass porosity reference standard;
    testing said porosity reference standard with on site ultrasonic instrumentation of an inspection site to obtain said attenuation of said ultrasonic signal;
    standardizing said on site ultrasonic instrumentation;
    manufacturing at least one additional porosity reference standard to include a porosity of a second spatially uniform level created within, wherein said second level of said porosity is different from said first level;
    testing said at least one additional porosity reference standard with said on site ultrasonic instrumentation to obtain attenuation of the ultrasonic signal;
    manufacturing a porosity reference standard that is porosity free; and
    testing said porosity free porosity reference standard with said on site ultrasonic instrumentation to obtain attenuation of the ultrasonic signal.

19. The porosity standardization process for ultrasonic inspection of composite materials of claim 17, further including the steps of:
    creating a three-dimensional computer aided design model that replicates voids forming a porosity within said composite material;

loading said three-dimensional computer aided design model into a etching program of an laser engraving machine;

placing said glass block into said laser engraving machine;

directing said laser beam according to said three-dimensional computer aided design model;

penetrating said glass block with said laser beam to create cracks; and repeating to penetrate said glass block with said laser beam until the three-dimensional computer aided design model is etched into said glass block.

20. The porosity standardization process for ultrasonic inspection of composite materials of claim 17, further including the steps of:

manufacturing said porosity reference standard to include at least a first area having a first porosity level and a second area having a second porosity level, and a third area that is porosity free; and testing said first area, said second area, and said third area of said porosity reference standard with said on site ultrasonic instrumentation to obtain attenuation of the ultrasonic signal;

obtaining a correction factor for said ultrasonic instrumentation; and inspecting composite laminate parts of an aircraft using said standardized on site ultrasonic instrumentation.

\* \* \* \* \*